(12) United States Patent
Hamann et al.

(10) Patent No.: US 8,643,390 B2
(45) Date of Patent: Feb. 4, 2014

(54) CORROSION SENSORS

(71) Applicant: International Business Machines Corporation, Armonk, NY (US)

(72) Inventors: Hendrik F. Hamann, Yorktown Heights, NY (US); Levente I. Klein, Tuckahoe, NY (US); Michael Alan Schappert, Wappingers Falls, NY (US); Prabjit Singh, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/760,391

(22) Filed: Feb. 6, 2013

(65) Prior Publication Data

US 2013/0149195 A1    Jun. 13, 2013

Related U.S. Application Data

(62) Division of application No. 12/854,416, filed on Aug. 11, 2010, now Pat. No. 8,390,306.

(51) Int. Cl.
*G01R 27/08* (2006.01)

(52) U.S. Cl.
USPC ............................. 324/700; 204/404; 204/412

(58) Field of Classification Search
USPC ................. 324/700; 204/404, 412; 205/775.5
See application file for complete search history.

(56) References Cited

U.S. PATENT DOCUMENTS

| | | | |
|---|---|---|---|
| 5,139,627 A | 8/1992 | Eden et al. | |
| 6,132,593 A | 10/2000 | Tan | |
| 6,683,463 B2 | 1/2004 | Yang et al. | |
| 6,982,519 B2 | 1/2006 | Guillorn et al. | |
| 7,982,474 B1 | 7/2011 | Hefner et al. | |
| 2004/0155670 A1* | 8/2004 | Yang et al. | 324/700 |
| 2009/0121872 A1 | 5/2009 | Lynch et al. | |
| 2009/0124025 A1 | 5/2009 | Hamilton et al. | |
| 2009/0195260 A1 | 8/2009 | Bell et al. | |
| 2012/0007617 A1* | 1/2012 | Fisseler et al. | 324/700 |

OTHER PUBLICATIONS

Ashrae Whitepaper, "Gaseous and Particulate Contamination Guidelines for Data Centers," http://www.ashrae.org/docLib/20090812_WhitePaper_ParticulateDatacomBk.pdf, 13 pages, Feb. 6, 2013.

K.T. Chiang et al., "A Nanostructured, Field Effect Transistor-Based Sensor," Proc. Corrosion 2007, Conf. Paper No. 7390, TX, NACE International 2007, 11 pages, Houston.

(Continued)

*Primary Examiner* — Vincent Q Nguyen

(74) *Attorney, Agent, or Firm* — Vazken Alexanian; Ryan, Mason & Lewis, LLP

(57) ABSTRACT

Corrosion sensor apparatus for detection of contamination affecting metal based components and devices. For example, an apparatus includes: a set of corrosion sensor elements, wherein a width of a first corrosion sensor element is different than a width of a second corrosion sensor element, wherein each corrosion sensor element is susceptible to corrosion caused by an operating environment of the corrosion sensor elements; and a set of reference elements wherein a width of a first reference sensor element is substantially equal to the width of the first corrosion sensor element and a width of a second reference sensor element is substantially equal to the width of the second corrosion sensor element, wherein each reference sensor element is not substantially susceptible to corrosion caused by the operating environment of the corrosion sensor elements.

5 Claims, 5 Drawing Sheets

(56) References Cited

OTHER PUBLICATIONS

N. Saedi et al., "Design and Fabrication of Corrosion and Humidity Sensors for Performance Evaluation of Chip Scale Hermetic Packages for Biomedical Implantable Devices," EMPC, Jun. 2009, pp. 1-4.

C.O. Muller et al., "Nanostructure—Based Device Detects and Monitors Corrosion," SPIE Newsroom, May 4, 2007, 2 pages.

* cited by examiner

BEFORE CORROSION

CORROSION

CORROSION SENSORS

CROSS-REFERENCE TO RELATED APPLICATION

The present application is a divisional of U.S. patent application Ser. No. 12/854,416, filed on Aug. 11, 2010, the disclosure of which is incorporated herein by reference in its entirety.

FIELD

The present application relates to detection of gaseous contamination affecting metal-based components, artifacts and devices such as electrical and electronic components and devices, and more particularly to corrosion sensors providing such detection.

BACKGROUND

Many facilities and buildings like museums, archives, clean rooms, data centers, or pharmaceutical labs require tight control on air quality (dust and gaseous contamination). Extensive effort is devoted to reduce air contamination and maintain safe operating conditions. Atmospheric contamination is known to exhibit geographical and temporal variations since it is closely tied to local human pollution activities such as power production, agriculture, transport, etc. To overcome atmospheric pollution in the above mentioned facilities and the like, air filtration and air recirculation/conditioning is commonly employed.

Data centers are known to be one of the most energy intensive types of facilities that require controlled atmosphere. A data center is a facility used to host computing systems (e.g., servers) and associated components, such as telecommunications and storage systems. A data center also generally includes redundant or backup power supplies, redundant data communications connections, environmental controls (e.g., air conditioning, fire suppression) and security devices. One environmental control approach provides for obtaining and utilizing outside air (i.e., outdoor air) to cool and to control the temperature of hardware associated with the computing systems of a data center.

However, the outside air cooling approach increases concerns of the presence of gaseous contaminants in data centers caused by the introduction of outside air. For example, pollution in the outside air introduces gaseous contaminants that attack (corrode) copper lines on circuit boards, individual components, or silver based soldering joints. Sulfur-bearing gases such as $SO_2$ and $H_2S$, nitrogen-based gases such as NO and $NO_2$, or reaction with toxic gases such as $Cl_2$ and Br can result in corrosion products being formed. The concentration of these gases are in the range of parts per billion (ppb), however, large temporal variations over the same geographical area can be commonly encountered due to weather, geography and economic activities. The indoor gaseous pollutants can be related to the outdoor gaseous concentration, as more polluted regions will have a higher indoor contamination. Thus, by way of example, for cooper lines on a circuit board, copper-sulfide is formed which creeps over the circuit board and short circuits closely spaced lines. For silver based soldering joints, silver-sulfide is formed which eats away at the silver, causing open circuits. Furthermore, airborne dust is also known to chemically corrode printed circuit board components.

A recent American Society of Heating, Refrigerating, and Air-Conditioning Engineers (ASHRAE) recommendation entitled "Gaseous and Particulate Contamination Guidelines for Data Centers," Aug. 2009, the disclosure of which is incorporated by reference herein in its entirety, set an upper limit of an acceptable corrosion level in data centers at 30 nanometers per month (nm/month) for both copper and silver.

SUMMARY

Illustrative embodiments of the invention provide methods and apparatus for detection of contamination affecting metal-based components, artifacts and devices such as electrical and electronic components and devices, and more particularly to corrosion sensors providing such detection.

For example, in a first embodiment of the invention, an apparatus comprises: a set of corrosion sensor elements comprising a first corrosion sensor element and at least a second corrosion element, each corrosion sensor element being coupled between a source and a monitor, wherein a width of the first corrosion sensor element is different than a width of the second corrosion sensor element, wherein each corrosion sensor element is susceptible to corrosion caused by an operating environment of the corrosion sensor elements; and a set of reference elements comprising a first reference sensor element and at least a second reference sensor element, each reference sensor element being coupled between the source and the monitor, wherein a width of the first reference sensor element is substantially equal to the width of the first corrosion sensor element and a width of the second reference sensor element is substantially equal to the width of the second corrosion sensor element, wherein each reference sensor element is not substantially susceptible to corrosion caused by the operating environment of the corrosion sensor elements.

In one example, a signal generated from the first corrosion sensor element in response to the source is received by the monitor and is compared to a signal generated from the first reference sensor element in response to the source and received by the monitor, wherein the result of the comparison is indicative of an amount of corrosion experienced by the first corrosion sensor element for a first period of time. Further, a signal generated from the second corrosion sensor element in response to the source is received by the monitor and is compared to a signal generated from the second reference sensor element in response to the source and received by the monitor, wherein the result of the comparison is indicative of an amount of corrosion experienced by the second corrosion sensor element for a second period of time.

Furthermore, each of the corrosion sensor elements is preferably formed such that the corrosion sensor element corrodes in a single spatial dimension (e.g., width). The single spatial dimension corrosion advantageously yields a linear response from the apparatus.

In a second embodiment of the invention, an apparatus comprises: a first sensor element; and at least a second sensor element; wherein the first sensor element and the at least a second sensor element are susceptible to corrosion caused by an operating environment in which they reside, and wherein the at least a second sensor element has a corrodible spatial dimension that is progressively larger than a corrodible spatial dimension of the first sensor element such that the at least a second sensor element provides for corrosion monitoring for a time period that is progressively larger than a period of time for corrosion monitoring associated with the first sensor element.

In a third embodiment of the invention, an apparatus comprises: a first corrosion sensor; a second corrosion sensor; and at least a third corrosion sensor; wherein the first, second, and third corrosion sensors are configured in a bridge arrangement such that when none of the first, second, and third corrosion sensors experiences corrosion, the bridge arrangement is in a balanced condition, and when at least one of the first, second, and third corrosion sensors experiences corrosion, the bridge arrangement is in an unbalanced condition. Each of the first, second and third corrosion sensors may comprise a first pair of thin film sensor elements that are exposed to corrosion and a second pair of thin film sensor elements that are not exposed to corrosion such that the amount of unbalance is directly related to corrosion of a width of the exposed sensor elements and a corrosion rate associated with the exposed sensor elements. Widths of the thin film sensor elements for each of the first, second and third corrosion sensors may progressively increase. The progressively increasing widths of the sensor elements provides for corrosion monitoring over progressively increasing time periods.

In a fourth embodiment of the invention, a method for fabricating a corrosion sensor device comprises the following steps. On a substrate, a set of corrosion sensor elements is formed comprising a first corrosion sensor element and at least a second corrosion element, each corrosion sensor element being coupled between a source and a monitor, wherein a width of the first corrosion sensor element is different than a width of the second corrosion sensor element, wherein each corrosion sensor element is susceptible to corrosion caused by an operating environment of the corrosion sensor elements. Further, on the substrate, a set of reference elements is formed comprising a first reference sensor element and at least a second reference sensor element, each reference sensor element being coupled between the source and the monitor, wherein a width of the first reference sensor element is substantially equal to the width of the first corrosion sensor element and a width of the second reference sensor element is substantially equal to the width of the second corrosion sensor element, wherein each reference sensor element is not substantially susceptible to corrosion caused by the operating environment of the corrosion sensor elements.

Advantageously, illustrative embodiments of the invention provide a resistive sensor with a linear response to corrosion that can be deployed for real time measurement of corrosion with high sensitivity and also over an extended period of time. These sensors could be deployed for real-time monitoring of the corrosion caused by contaminations attributed to both inside and outside environment and they could be deployed as integral parts of the air cooling process. Such inventive corrosion sensors overcome sensitivity problems with existing sensor designs, as well as non-linearity problems whereby the response of existing sensors is non-linear as corrosion proceeds both from top to bottom and from the sides of the metal film, thus making data interpretation difficult and inaccurate.

These and other objects, features, and advantages of the present invention will become apparent from the following detailed description of illustrative embodiments thereof, which is to be read in connection with the accompanying drawings.

DETAILED DESCRIPTION

Figure 1:
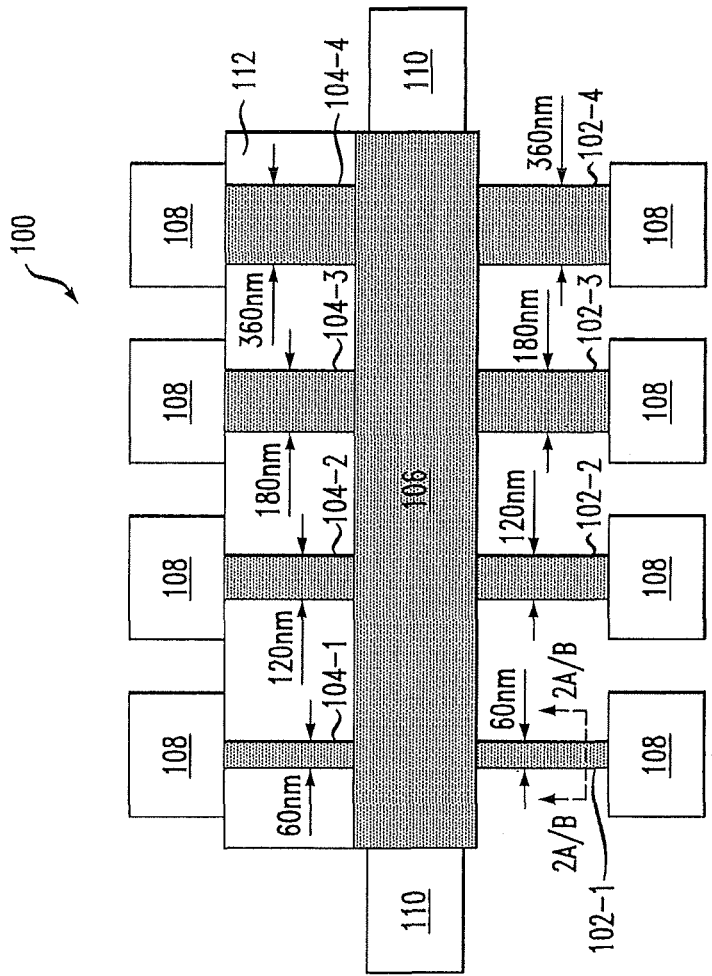
FIG. 1 illustrates a top view of a corrosion sensor, according to an embodiment of the invention.

Illustrative embodiments of the invention may be described herein in the context of detecting atmospheric contaminants in data center environments. However, it is to be understood that the techniques of the invention are not limited to use in data centers but are more broadly applicable to detection of corrosive contaminants affecting any electrical and electronic components and devices. Furthermore, such inventive corrosion sensors can be used to monitor corrosion of any suitable types of metal-based components, artifacts and devices that are susceptible to corrosion.

As will be explained in detail herein, illustrative embodiments of the invention provide a metal film resistor based corrosion sensor with a linear response that is capable of sensing corrosion rates down to a sensitivity of approximately zero nm/month. The sensors are optimized to work on a relatively low corrosion rate with corrosion product formed at a rate of about 30 nanometers/month or lower. A "thin metal film" or "metal film" is an example of a "sensor element" that may be employed by the corrosion sensor of the invention. The metal film (e.g., silver film, copper film, etc.) is also referred to herein as a "metal wire" and may alternatively be considered a "nanowire." Metal films are current conducing elements with a resistance characteristic that is dependent on their spatial dimensions. It is to be appreciated that the spatial dimensions of the sensor elements used in accordance with the invention are dependent on the type of corrosion being detected and the duration of the time period intended for detection. Thus, corrosion sensor principles of the invention are not intended to be limited to any specific spatial dimensions or specific range of spatial dimensions.

Rather, the sensor according to illustrative embodiments has multiple corrosion sensitive resistor arms with progressively increasing widths that can be used to sense the corrosive environment for an extended period of time with the same high sensitivity by selectively changing the sensing arm of the sensor being monitored. The metal film (wire) based resistors change their resistance as corrosion proceeds from the sides of the film or wire, while the top of the film or wire is protected with a corrosion resistive material, as will be explained in detail below. This ensures a linear response for the inventive sensor.

Highly sensitive corrosion sensors, such as those described herein in accordance with principles of the invention, are advantageous for use in gaseous contamination monitoring in museums, hospitals, and data centers so as to mitigate and control the amount of outside air allowed in such facilities. That is, when a certain level of corrosion is detected via the sensor response, the cooling environment of the facility can be correspondingly regulated to reduce the cause of the corrosion level, i.e., gaseous contaminants in the outside air supply used in the facility cooling process. This may be accomplished by filtering techniques, or cutting back or even eliminating outside air for use in cooling components of the facility.

FIG. 1 illustrates a top view of a multi-metal film corrosion sensor, according to an embodiment of the invention. As shown, corrosion sensor 100 comprises a set of multiple corrosion sensor elements 102-1 through 102-4, with progressively increasing widths. The corrosion sensor elements 102 are in the form of metal films, although other suitable sensor elements may be employed. The corrosion sensor 100 also comprises a set of reference sensor elements 104-1 through 104-4, with progressively increasing widths. The reference sensor elements 104 are also in the form of metal films, although other suitable sensor elements may be employed. Note that the width of the corrosion sensor element 102-1 is equal to (or approximately or substantially equal to) the width of the reference sensor element 104-1. The same is true for sensor elements 102-2 and 104-2, for sensor elements 102-3 and 104-3, and for sensor elements 102-4 and 104-4. The rationale for this will be explained below.

As further shown in FIG. 1, the corrosion sensor 100 also comprises a connecting bus 106. The connecting bus 106 is composed of the same metal (electrical conducting material) as the variable width sensor elements (102 and 104). The connecting bus 106, like the reference sensor elements but unlike the corrosion sensor elements, has a conductive coating to protect it from corrosion.

While not visible in FIG. 1 (but which is visible in FIG. 2 as 206), the corrosion sensor 100 also comprises a substrate. The substrate may be any substantially non-conducting material, by way of example only, glass or glass-based, or silicon or silicon-based. The substrate maintains the sensor elements 102 and 104, the connecting bus 106, and contact pads 108 and 110 in place so that they remain electrically connected, as will be explained. In one embodiment, the various components of the corrosion sensor 100 are formed on top of the substrate via well-known electron beam lithography fabrication processes.

Contact pads 108 are electrically conductive pads to which the sensor elements 102 and 104 are respectively connected. That is, each sensor element 102 and 104 has one of its ends connected to its own dedicated contact pad 108. Contact pads 108 are then connected to a current or voltage reading device (i.e., monitor) so that a current signal or voltage signal can be received by the monitor. As will be explained below, these signals are used to detect the level of corrosion being experienced by the corrosion sensor 100.

Contact pads 110 are also electrically conductive pads which connect to the connecting bus 106. Thereby, the sensor elements 102 and 104 are respectively connected to the contact pads 110. In this case, each sensor element 102 and 104 has the other one of its ends connected to one contact pad 110 (via connecting bus 106) that is itself connected to a voltage supply source V. The other contact pad 110 is connected to a ground potential. Thus, one contact pad 110 is grounded while the current from contact pad 108 is going to a detection circuit that can be a trans-impedance amplifier or voltage detector.

Also shown in FIG. 1, the corrosion sensor 100 comprises an encapsulation layer 112. Encapsulation layer 112 encapsulates the reference sensor elements 104-1 through 104-4 and the connecting bus 106 to protect them from the corrosive atmospheric environment to which the corrosion sensor elements 102-1 through 102-4 are exposed. The encapsulation layer 112 may be formed from materials such as thick dielectric film that is inert to corrosion, e.g., $SiO_2$, $Si_3N_4$, or organic coatings like polystyrene or other corrosion resistant materials.

In accordance with this illustrative embodiment, the corrosion sensor 100 operates such that the resistance of each corrosion sensor element 102, in this case, each metal film (wire) 102, changes due to a reduced conduction path as the width of the metal film is converted from a metal to a nonconductive oxide due to corrosion. As the corrosive gases in the atmospheric environment, in which the sensor 100 operates, attack the metal of the metal film and transform it to a nonconductive oxide, the width is reduced thus increasing the resistance of the metal film.

The sensor elements 102 and 104 of the corrosion sensor 100 are preferably fabricated by electron beam lithography. Further, the connecting bus 106 may be formed that has arms (sensor elements) extending along the sides, such as is illustrated in FIG. 1. The sensor elements have variable (progressively increasing) widths and the width of each sensor element determines the lifetime of the sensor element.

As an example, as shown in FIG. 1, the progressively-increasing widths of the sensor elements 102 and 104 can be fabricated to be about 60 nm (sensor elements 102-1 and 104-1), about 120 nm (sensor elements 102-2 and 104-2), about 180 nm (sensor elements 102-3 and 104-3), and about 360 nm (sensor elements 102-4 and 104-4) wide. For a corrosion rate of 30 nm/month (recall the ASHRAE recommendation mentioned above), the 60 nm wide sensor element (102-1) could be used for corrosion monitoring for a time duration of one month, while the 120 nm wide sensor element (102-2) would be usable for a two month period, and the 180 nm wide sensor element (102-3) would be usable for a three month period. Although not expressly illustrated in FIG. 1, there could be 240 nm and 360 nm wide corrosion sensor elements for use for time durations of four and five months, respectively. The 360 nm wide sensor element (102-4) would be usable for a six month period. Of course, shorter/longer individual time intervals can be achieved simply by decreasing/increasing the progressively-increasing widths. Likewise, less/more time durations can be achieved simply by subtracting/adding corrosion sensitive resistor arms.

It is to be appreciated that the reduced width assures that the changes associated with a relatively small corrosion rate can be easily detected as the change in width is significant compared with the total width. The width of the sensor elements can be fabricated according to the expected corrosion rate in the environment and, in this embodiment, would be twice as large as the expected corrosion thickness due to corrosion proceeding from both sides.

Figure 2A:
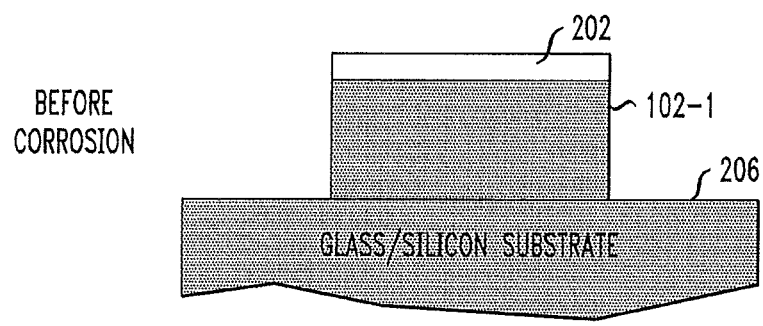
FIG. 2A illustrates a cross section view of a corrosion sensitive resistor arm of a corrosion sensor before corrosion, according to an embodiment of the invention.
Figure 2B:
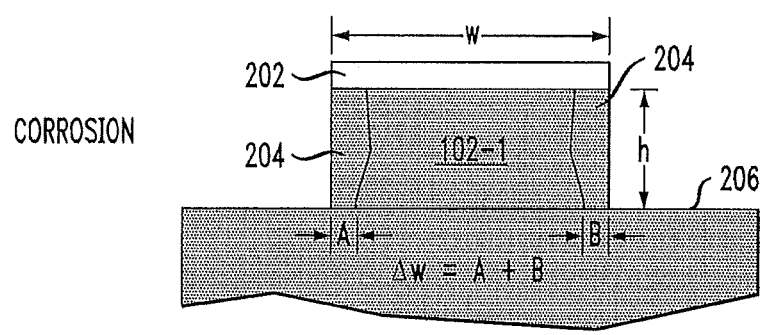
FIG. 2B illustrates a cross section view of a corrosion sensitive resistor arm of a corrosion sensor during or after corrosion, according to an embodiment of the invention.

This operation is illustrated in the context of FIGS. 2A and 2B, where FIG. 2A illustrates a cross section view of a corrosion sensitive resistor arm of a corrosion sensor before corrosion, and FIG. 2B illustrates a cross section view of a corrosion sensitive resistor arm of a corrosion sensor during or after corrosion. The particular corrosion sensitive resistor arm shown in FIGS. 2A and 2B is the arm that includes corrosion sensor element 102-1 (note the cross section line 2A/B in FIG. 1); however, this is for illustration purposes only and each corrosion sensitive resistor arm of the sensor 100 is formed and operates in a similar manner as described herein.

As shown, in FIGS. 2A and 2B, a protective film 202 is formed on the top of corrosion sensor element 102-1. Note that as shown here in the subject figures, the sensor element 102-1 is formed on top of the non-conductive substrate 206. The protective film 202 can be formed from such material as $Al_2O_3$ (aluminum oxide) or $Si_3Ni_4$ (silicon nitride). It is to be understood that the protective layer 202 is preferably formed via the electron-beam fabrication process that is used for the deposited metal film (sensor elements). The protective film may be also be made of the same material as the encapsulation layer 112 (recall that the encapsulation layer encapsulates the reference sensor elements 104 and the conducting bus 106).

Thus, note that for the corrosion sensor element 102, the protective film coating covers the top of the sensor element (as shown in FIG. 2A), but in the case of the reference sensor elements 104, the protective film (encapsulation layer) covers both the top and the sides of the metal film resistors such that they are fully protected from corrosion. This is also the case for the conducting bus 106 so that it is fully protected from corrosion. Note that the bottoms of the sensor elements 102 and 104, and the conducting bus 106 are protected from corrosion by the substrate 206.

More specifically, the protective film 202 shown in FIG. 2A serves to prevent the corrosion sensor element 102-1 from corroding in a spatial dimension other than width w. That is, since the height h of the sensor element 102-1 is contained by the substrate 206 on one end and the protective film 202 on the other end, as the sensor element is exposed to contaminants, it corrodes in a single spatial dimension, i.e., width w. That is what reference numeral 204 denotes, i.e., corroded lateral sides 204. Thus, the two respective sides of the sensor element 102-1 corrode an amount denoted by A and B, and this is what Δw represents (A plus B).

The resistance R of a given metal film (wire) prior to corrosion (in this case, corrosion sensor element 102-1 in FIG. 2A) is represented as:

$$R = \rho \frac{L}{wh} \quad \text{Eq. (1)}$$

where w is the width of the sensor element, h is the height of the sensor element (wh denoting the area of the metal film), L is the length of the sensor element, and p is the electrical resistivity (also known as specific electrical resistance or volume resistivity) of the sensor element. Electrical resistivity is a measure of how strongly a material opposes the flow of electric current (measured in ohm meters).

The resistance $R_{corr}$ of a given metal film after or during corrosion (in this case, corrosion sensor element 102-1 in FIG. 2B) is represented as:

$$R_{corr} = \rho \frac{L}{(w - \Delta w)h} \quad \text{Eq. (2)}$$

where Δw represents A plus B (i.e., the corroded width from both lateral sides of the metal film).

Recall from FIG. 1 that the reference sensor elements 104 are encapsulated via encapsulation layer 112 so as not to be affected by corrosive contaminants. Thus, the resistance R of each of these metal films (wires) will remain substantially constant and thus be represented by Eq. (1). That is, there is no Δw associated with the reference sensor elements 104.

Note that while FIGS. 2A and 2B show corrosion effects for corrosion sensor element 102-1, the same corrosion effects and resulting equations apply to the other corrosion sensor elements (102-2, 102-3, etc.).

A measurement operation of the corrosion sensor 100 will now be explained in the context of FIG. 3. A constant voltage V is applied to one end of the sensor 100 (at contact pad 110) and the current passes through the connecting bus 106 to each of the variable width arms of the sensor 100. The current passing through each sensor element (each variable width arm) is monitored. For example, in one embodiment, the current may be converted to voltage using a transimpedance amplifier (not shown, but generally depicted as monitor(s) in FIG. 3) where the resulting voltage is proportional to the width of the metal films (wires). As corrosion proceeds, each sensor element 102 corrodes laterally and its resistance increases as per Eq. (2), i.e., as Δw increases, the denominator of Eq. (2) gets smaller, and the resistance $R_{corr}$ increases.

Thus, in accordance with the present invention, by measuring the current flowing through corrosion sensor element 102-1 and measuring the current flowing through the reference sensor element 104-1, and comparing the two measurements, the result will be directly proportional to the corrosion thickness.

Figure 3:
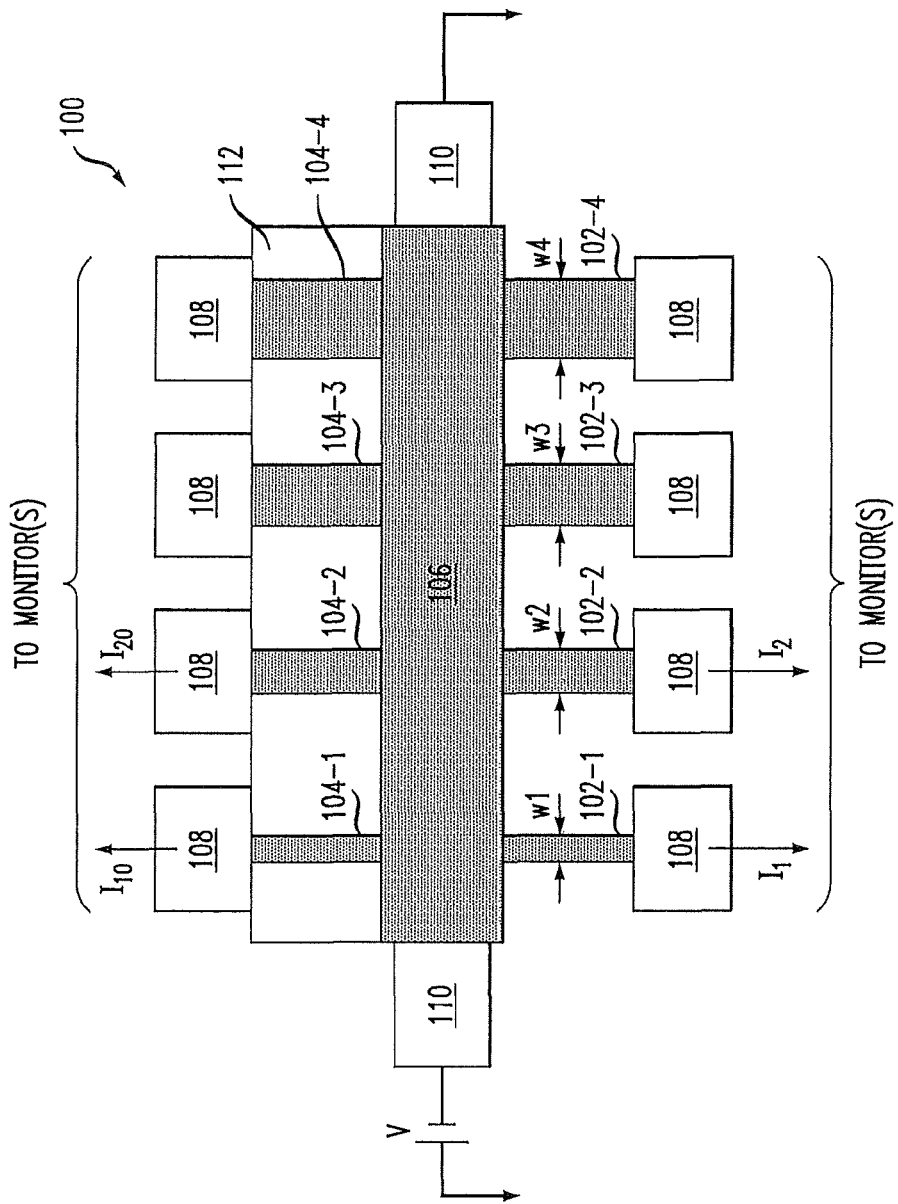
FIG. 3 illustrates a top view of a measurement setup for a corrosion sensor, according to an embodiment of the invention.

That is, as shown in FIG. 3, the current measured from reference sensor element 104-1 is:

$$I_{10} = \frac{V}{R_{10}} = V \frac{w_1 h}{\rho L} \quad \text{Eq. (3)}$$

while the current measured from reference sensor element 104-2 is:

$$I_{20} = \frac{V}{R_{20}} = V \frac{w_2 h}{\rho L} \quad \text{Eq. (4)}$$

Furthermore, the current measured from corrosion sensor element 102-1 is:

$$I_1 = \frac{V}{R_1} = V \frac{(w_1 - \Delta w)h}{\rho L} \quad \text{Eq. (5)}$$

while the current measured from corrosion sensor element 102-2 is:

$$I_2 = \frac{V}{R_2} = V \frac{(w_2 - \Delta w)h}{\rho L} \quad \text{Eq. (6)}$$

Thus, at beginning before corrosion effects are present (FIG. 2A), the difference between, for example, the current from the corrosion sensor element 102-1 and the reference sensor element 104-1 ($I = I_1 - I_{10}$) is zero. However, as corrosion proceeds (FIG. 2B), the current difference changes linearly, as the width of the corrosion sensor element 102-1 decreases. The maximum current would be when the corrosion sensor element is fully corroded. This may be denoted as:

$$I = I_1 - I_{10} = V \frac{\Delta w h}{\rho L} \quad \text{Eq. (7)}$$

Advantageously, the current I represents the rate of corrosion for the particular corrosion sensitive resistor arm being monitored. It is to be appreciated that this same signal measurement and comparison applies to each pair of reference and corrosion sensor elements.

All elements are connected to detection circuitry (a monitor) and they will record the corrosion rate as it proceeds for all of the different widths metal films. The parallel measurement allows for correlation of the corrosion rate from all the different width sensors. The same rate will be measured by all of the sensors. As expected, the widest sensor will have the longest operational lifetime.

Figure 4:
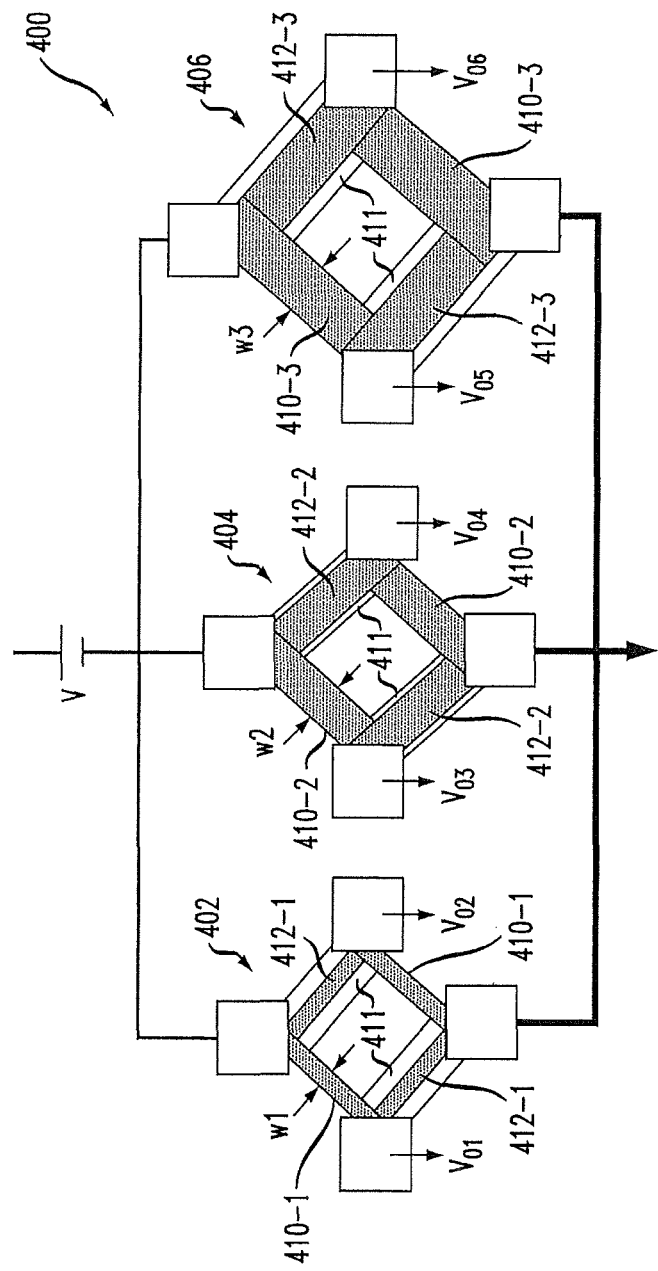
FIG. 4 illustrates a top view of a bridge detection setup for a corrosion sensor, according to an embodiment of the invention.

To enhance the sensitivity of a corrosion sensor detection to be able to monitor small a corrosion rate, a corrosion sensor can be integrated in a bridge circuit setup as illustrated in FIG. 4.

As shown, the bridge setup 400 comprises three corrosion sensors 402, 404 and 406 (although more or less sensors can be employed). Each corrosion sensor is comprised of two thin film sensor elements (metal films or wires) that are exposed to corrosion (410-1 in sensor 402; 410-2 in sensor 404; and 410-3 in sensor 406) and two thin film sensor elements (metal films or wires) that are covered with conformal coating 411 (i.e., similar material as encapsulation layer 112 and protective film 202) so as not to be exposed to corrosion (412-1 in sensor 402; 412-2 in sensor 404; and 412-3 in sensor 406). The conformal coated sensor elements are the reference sensor elements while two other sensor elements are exposed to the corrosive environment and their resistance will change as the width of the thin film decreases. The widths of the sensor elements for each corrosion sensors 402, 404 and 406 (i.e., w1, w2 and w3) progressively increase. This provides the progressive time period corrosion monitoring explained above with respect to the corrosion sensor in FIG. 3.

At the beginning, all the sensor elements in a given corrosion sensor have the same value and the bridge circuit 400 is balanced, i.e., the differential voltage from the two node points (V01 and V02 for sensor 402; V03 and V04 for sensor 404; and V05 and V06 for sensor 406) is zero. However, small changes in the resistance value of the sensor elements not conformally coated will take the bridge circuit out of balance. The bridge can be operated under constant voltage V that would decrease the current flowing through each corrosion sensor circuit as the corrosion resistance value increases. The bridge circuit 400 advantageously allows a two fold increase in resistance change sensitivity detection.

Advantageously, in this particular embodiment, the bridge circuit arrangement of FIG. 4 is constructed such that all the parts of the sensors (402, 404, and 406) are fabricated from the same metal having two opposite elements of the bridge exposed to the corrosive environment while the two other elements are protected from the corrosive atmosphere by a protective coating. For a corrosion sensor in the bridge circuit arrangement, all four sensor elements are equal in size such that when none of the corrosion sensors experiences corrosion, the bridge arrangement is in a balanced condition, and when at least one of the corrosion sensors experiences corrosion, the bridge arrangement is in a unbalanced condition. Since all the elements of the bridge circuit are from the same metal deposited on the same substrate, the temperature variation that can cause resistance changes are advantageously eliminated.

Figure 5:
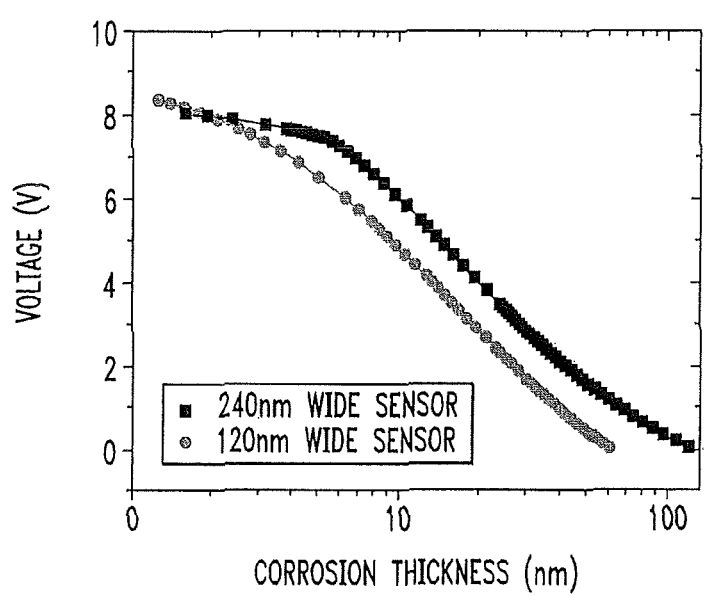
FIG. 5 illustrates detection sensitivity for sensor elements, according to an embodiment of the invention.

As an example, the detection sensitivity for 120 nm and 240 nm wide sensors (which are actually 60 nm and 120 nm, respectively, as the corrosion proceeds from both sides) is shown in FIG. 5. Both sensors have sufficient dynamic range so as to be able to detect variation down to about 0.1 nm variation in film width.

Furthermore, in an integrated circuit implementation of the invention, multiple integrated circuit dies are typically formed in a repeated pattern on a surface of a wafer. Each such die may include a device comprising corrosion detection circuitry as described herein, and may include other structures or circuits. Still further, in another embodiment, the corrosion detection circuitry could be implemented in multiple dies and in multiple integrated circuit packages. In any case, the dies are cut or diced from the wafer, then packaged as integrated circuits. One skilled in the art would know how to dice wafers and package dies to produce packaged integrated circuits. Integrated circuits so manufactured are considered part of this invention. Thus, methods for forming one or more of the components of a corrosion sensor device as described herein are within the scope of the invention.

Accordingly, as has been illustratively described herein, principles of the invention provide a corrosion sensor with a linear response, as the corrosion proceeds, combined with ultra low corrosion rate sensitivity (e.g., 10 nm/month). The sensor is based on the width reduction of a metal film (wire) exposed to a corrosive environment and its response is compared to a reference resistor that is shielded from the corrosive environment. Employing different width metal films (wires) the sensor can be deployed over an extended period of time while maintaining the same corrosion sensitivity. The sensor can be deployed both for monitoring internal and external environmental conditions in real time.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. An apparatus, comprising:
a first sensor element; and
at least a second sensor element;
wherein the first sensor element and the at least a second sensor element are susceptible to corrosion caused by an operating environment in which they reside, and wherein the at least a second sensor element has a corrodible spatial dimension that is progressively larger than a corrodible spatial dimension of the first sensor element such that the at least a second sensor element provides for corrosion monitoring for a time period that is progressively larger than a period of time for corrosion monitoring associated with the first sensor element.

2. The apparatus of claim 1, wherein the corrodible spatial dimension is width.

3. The apparatus of claim 2, wherein the width of the at least a second sensor element is about two times a width of the first sensor element.

4. The apparatus of claim 3, further comprising at least a third sensor element that is susceptible to corrosion caused by an operating environment in which the sensor elements reside, and wherein the at least a third sensor element has a corrodible spatial dimension that is progressively larger than the corrodible spatial dimension of the second sensor element.

5. The apparatus of claim 1, wherein a corrosion rate associated with the first sensor element is equivalent to about half of the corrodible spatial dimension of the first sensor element.

* * * * *